United States Patent
Lee et al.

(10) Patent No.: US 10,631,747 B2
(45) Date of Patent: Apr. 28, 2020

(54) MEASUREMENT PATCH DEVICE

(71) Applicant: Shuenn-Yuh Lee, Tainan (TW)

(72) Inventors: Shuenn-Yuh Lee, Tainan (TW); Jia-Ren Chiou, Tainan (TW)

(73) Assignee: Shuenn-Yuh Lee, Tainan (TW)

( * ) Notice: Subject to any disclaimer, the term of this patent is extended or adjusted under 35 U.S.C. 154(b) by 1145 days.

(21) Appl. No.: 14/991,946

(22) Filed: Jan. 9, 2016

(65) Prior Publication Data
US 2016/0198972 A1    Jul. 14, 2016

(30) Foreign Application Priority Data

Jan. 12, 2015    (TW) .............................. 104100979 A (51) Int. Cl.
| | |
|---|---|
| *A61B 5/0408* | (2006.01) |
| *A61B 5/00* | (2006.01) |
| A61B 5/0478 | (2006.01) |
| A61B 5/0492 | (2006.01) |
| A61B 5/0496 | (2006.01) |
| A61B 5/021 | (2006.01) |
| A61B 5/053 | (2006.01) |
| A61B 5/04 | (2006.01) |

(52) U.S. Cl.
CPC ........ *A61B 5/04085* (2013.01); *A61B 5/6832* (2013.01); *A61B 5/6833* (2013.01); *A61B 5/0006* (2013.01); *A61B 5/0008* (2013.01); *A61B 5/021* (2013.01); *A61B 5/04001* (2013.01); *A61B 5/0492* (2013.01); *A61B 5/0496* (2013.01); *A61B 5/053* (2013.01); *A61B 2560/0412* (2013.01); *A61B 2560/0443* (2013.01); *A61B 2562/164* (2013.01)

(58) Field of Classification Search
CPC . A61B 5/04085; A61B 5/6833; A61B 5/0006; A61B 5/0008; A61B 5/04001; A61B 5/0492; A61B 5/0496; A61B 5/053; A61B 5/6832; A61B 5/68335; A61B 2560/0412; A61B 2560/0443; A61B 2562/164
See application file for complete search history.

(56) References Cited

U.S. PATENT DOCUMENTS

| | | | | |
|---|---|---|---|---|
| 5,465,715 A | * | 11/1995 | Lyons ................ | A61B 5/04087 600/391 |
| 5,788,633 A | * | 8/1998 | Mahoney ........... | A61B 5/04085 600/382 |
| 5,995,861 A | * | 11/1999 | Price .................. | A61B 5/04085 600/372 |
| 7,037,114 B1 | * | 5/2006 | Eiger ................. | H01R 13/5224 439/67 |
| 9,326,695 B1 | * | 5/2016 | Kryzpow ........... | A61B 5/04085 |

(Continued)

*Primary Examiner* — Lee S Cohen
*Assistant Examiner* — Erin M Cardinal
(74) *Attorney, Agent, or Firm* — Chun-Ming Shih; Lanway IPR Services (57) ABSTRACT

A measurement patch device may change length according to somatotype of a user, and may be joined with another measurement patch device integrally according to the need of different physiological lead measurement. Moreover, the two joined measurement patch devices may rotate with respect to each other, such that multi-channel or multi-lead physiological signal may be measured to save measurement time of physiological signal.

9 Claims, 5 Drawing Sheets

(56) References Cited

U.S. PATENT DOCUMENTS

| | | | | |
|---|---|---|---|---|
| 2002/0019166 A1* | 2/2002 | Ubby | ............... | A61B 5/04085 |
| | | | | 439/505 |
| 2006/0058600 A1* | 3/2006 | Eichler | ............... | A61B 5/0536 |
| | | | | 600/407 |
| 2008/0288026 A1* | 11/2008 | Cross | ............... | A61B 5/0408 |
| | | | | 607/60 |
| 2009/0171163 A1* | 7/2009 | Mates | ............... | A61B 5/00 |
| | | | | 600/300 |
| 2011/0237922 A1* | 9/2011 | Parker, III | ............... | A61B 5/0006 |
| | | | | 600/382 |
| 2014/0343392 A1* | 11/2014 | Yang | ............... | A61B 5/04011 |
| | | | | 600/393 |

* cited by examiner

MEASUREMENT PATCH DEVICE

CROSS-REFERENCE TO RELATED APPLICATIONS

This application claims the priority of Republic of China Patent Application No. 104100979 filed on Jan. 12, 2015, in the State Intellectual Property Office of the R.O.C., the disclosure of which is incorporated herein by reference.

BACKGROUND OF THE INVENTION

Field of the Invention

The invention relates to a measurement patch device, more specifically to a measurement patch device that can change length.

Descriptions of the Related Art

The medical care level has been increased in recent years, so that there is a trend of technological development for measuring physiological signal of a human body anytime and anywhere. A measurement patch device is one of the most common equipments for measurement of physiological signal of a human body now. It has at least two electrodes attached to the human body for measurement of the physiological signal of the human body. Various health conditions of the human body are monitored by measurement of the physiological signal. The physiological signal is, e.g., EEG, ECoG, EKG, EMG or ECG physiological signal.

However, relative positions of the electrodes of the measurement patch device on the human body would influence correctness of the measured physiological signal. Therefore, in using the measurement patch device every time, the relative positions of the two electrodes have to be adjusted in accordance to sites on the human body to be measured by professional medical staff to obtain correct physiological signal, so that the measurement patch device cannot be used at home. In addition, the relative positions of the two electrodes of most measurement patch devices cannot be adjusted, so that only measurement of physiological signal for particular sites on the human body is applicable. Such defect is disadvantageous to users.

Therefore, people and vendors in the art are interested in providing a measurement patch device capable of adjusting the relative positions of the electrodes thereof.

SUMMARY OF THE INVENTION

In view of the shortages of the prior art above, the invention provides a measurement patch device having a first electrode and a second electrode attached to a first site and a second site on a human body, respectively, for measuring a physiological signal. The measurement patch device comprises a device body, a slipping body and a signal process module. The device body has a guide rail formed thereon and has a first electrode bonding portion and a first signal transfer layer. The first electrode bonding portion bonds the first electrode and connects electrically the first electrode and the first signal transfer layer. The slipping body is provided on the guide rail of the device body in a slipping manner for slipping on the device body. The slipping body has an accommodation space formed therein and further has a second electrode bonding portion and a second signal transfer layer. The second electrode bonding portion bonds the second electrode for the second electrode and the second signal transfer layer in electrical connection. The signal process module is accommodated in the accommodation space, acquiring the physiological signal measured by the first, second electrode through the first, second signal transfer layer, respectively, and processing, analyzing and wirelessly communicating the acquired physiological signal.

Optionally, the first, second electrode bonding portions are bonded with the first, second electrodes in a manner selected from the group of lock joint, fastening, magnetism and adhesion, respectively.

Optionally, the device body further has a first joining portion. The first joining portion is used to join the slipping body of another set of measurement patch devices for the first signal transfer layer of the device body to be in electrical connection with the second signal transfer layer of the slipping body of the another set of measurement patch devices. The slipping body further has a second joining portion. The second joining portion is used to join the first joining portion of another set of measurement patch devices for the second signal transfer layer of the slipping body to be in electrical connection with the first signal transfer layer of the another set of measurement patch devices. The first, second joining portions may be an elastic tenon or an engagement hole with fitting structure, respectively, for the two joined sets of measurement patch devices to rotate with respect to each other.

Optionally, the device body and the slipping body have a first identification mark and a second identification mark, respectively, for identifying an overlapping level of the slipping body on the device body. The device body has multiple positioning portions equidistantly for positioning the slipping body on the device body, such that the slipping level of the slipping body on the device body may be maintained.

In comparison with prior arts, a measurement patch device of the invention has a length adjustment structure capable of changing length according to the somatotype of a user for measurement of physiological signal for various sites on a human body, and of joining with another set of measurement patch devices integrally for measurement according to different physiological lead measurement needs, and having a rotational structure for the two mutually joined measurement patch devices to rotate with respect to each other under force, such that multi-channel or multi-lead physiological signal measurement is available to save physiological signal measurement time, so that the measurement patch device of the invention is applicable to making ECG (electrocardiogram) or other physiological signal, such as EEG, ECoG, EKG, or EMG physiological signal.

Moreover, an identification mark is also arranged for the measurement patch device of the invention in order to identify relative positions of a device body and a slipping body. As such, the relative positions of the two electrodes of the measurement patch device may be appropriate for effective subsequent measurement of physiological signal without assistance from professional medical staff, so that the measurement patch device of the invention may be used at home.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

The invention provides a measurement patch device with improved structure, which may be attached to a human body for measurement of physiological signal together with analysis, process, and wireless communication. The physiological signal may be, for example, electrocardiographic signal, temperature signal, blood pressure signal, impedance signal or nerve conduction signals etc., such as EEG, ECoG, EKG, or EMG physiological signal. In addition, the measurement patch device provided by the invention may change length to adjust relative positions of electrodes thereof in order for ease of accommodation and applicability of measurement for physiological signal from various sites on the human body.

For illustration with respect to features for the measurement patch device of the invention, refer to FIG. 1 to FIG. 11 in drawings in conjunction. As shown in the figures, the measurement patch device 1 of the invention has a first electrode 2 and a second electrode 3 on both front and back ends, respectively. The first, second electrodes 2, 3 may be attached to a first site, a second site on the human body, respectively, for measurement of the physiological signal from two different sites on the human body, respectively. The first, second electrodes 2, 3 have adhesive layers with, for example, electrically conductive silicone, such that attachment to the human body is available for measurement of the physiological signal.

Figure 1:
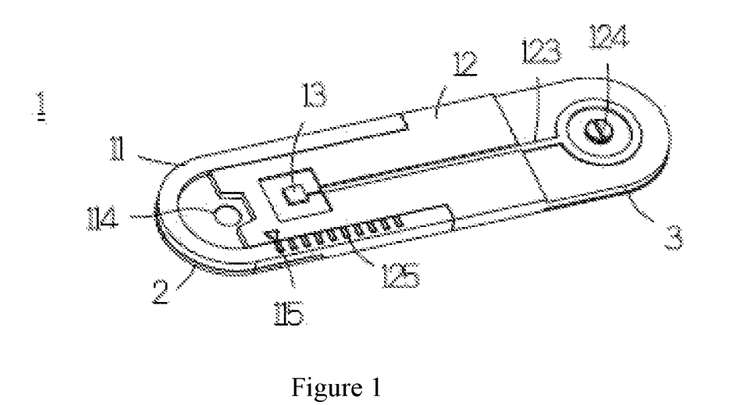
FIG. 1 is a stereogram showing an example of a measurement patch device according to the invention.
Figure 2:
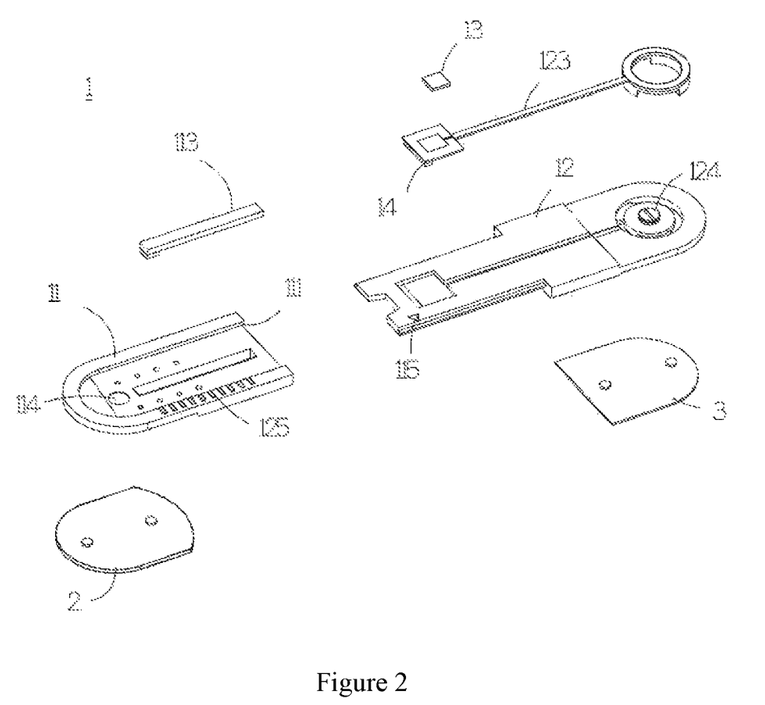
FIG. 2 is a breakdown drawing of the measurement patch device shown in FIG. 1.
Figure 5:
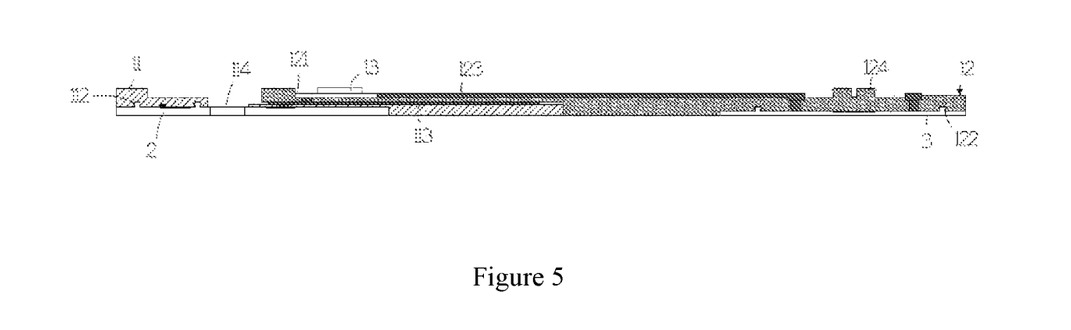
FIG. 5 is a cross-sectional view taken along line BB shown in FIG. 3.

The measurement patch device 1 may further comprise a device body 11, a slipping body 12 and a signal process module 13. The device body 11 and the slipping body 12 may be made of soft material, which may change shape in adaptation to measurement sites of the human body. The device body 11 shown in FIG. 5 is formed with a guide rail 111, and further has a first electrode bonding portion 112 and a first signal transfer layer 113 made of electrically conductive material. The guide rail 111 shown in FIG. 2 is a slot-like rail track provided concavely on the device body 11, but the arrangement form of the guide rail 111 on the device body 11 should not be limited thereto. For example, the guide rail 111 may also be provided convexly on the device body 11 to form a rail track with a bump form.

The first electrode bonding portion 112 has a bonding structure for bonding the first electrode 2, such that bonding with the first electrode 2 in a manner selected from the group of lock joint, fastening, magnetism and adhesion is available, so that after measurement of the physiological signal has been completed, the first electrode 2 may be dismounted from the first electrode bonding portion 112 for renewing or cleaning. In the example shown in FIG. 5, the first electrode bonding portion 112 is bonded with the first electrode 2 in a lock joint manner. The device body 11 or the first electrode bonding portion 112 further has an electrically conductive layer thereon for the first electrode 2 and the first signal transfer layer 113 to be in electrical connection, such that the physiological signal measured by the first electrode 2 may be transferred to the first signal transfer layer 113.

The slipping body 12 has a second electrode bonding portion 122 and a second signal transfer layer 123. The second electrode bonding portion 122 has a bonding structure for bonding a second electrode 3, such that bonding with the second electrode 3 in a manner selected from the group of lock joint, fastening, magnetism and adhesion is available, so that after measurement of the physiological signal has been completed, the second electrode 3 may be dismounted from the second electrode bonding portion 122 for renewing or cleaning. The slipping body 12 or the second electrode bonding portion 122 further has an electrically conductive layer thereon for the second electrode 3 and the second signal transfer layer 123 to be in electrical connection, such that the physiological signal measured by the second electrode 3 may be transferred to the second signal transfer layer 123.

The signal process module 13 is arranged in an accommodation space 121 of the slipping body 12 to slip with the slipping body 12 relative to the device body 11. The signal process module 13 may be in electrical connection with the first, second signal transfer layers 113, 123, respectively to acquire the physiological signal measured by the first, second electrodes 2, 3, and process and analyze the acquired physiological signal to get physiological information.

Figure 10:
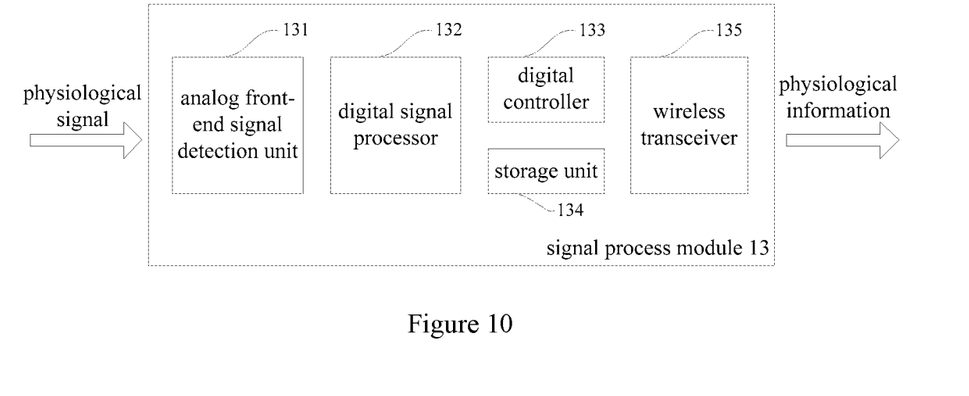
FIG. 10 is a schematic diagram showing one example for a signal process module of the invention.

In the example shown in FIG. 10, an analog front-end signal detection 131, a digital signal processor 132, a digital controller 133, a storage unit 134 and a wireless transceiver 135 may be arranged in the signal process module 13. The analog front-end signal detection unit 131 is used to acquire the physiological signal. The digital signal processor 132 is employed as feature extraction and classification of physiological signal for processing and analyzing the physiological signal to convert the physiological signal into digital physiological information. The digital controller 133 is used to provide communication between the digital signal processor and the wireless transceiver. The storage unit 134 is used to store the acquired physiological signal, and the processed and analyzed physiological information. The wireless transceiver 135 may send the acquired physiological signal and the processed and analyzed physiological information to a monitoring device by using a wireless communication technology, such as WIFI, Bluetooth, Zigbee, or a wireless transmission module developed by oneself. As stated above, the wireless transceiver is used to provide communication between the signal process module and the monitoring device.

The slipping body 12 of the invention further has a slipping structure designed in adaptation to the guide rail 111 and may be provided on the guide rail 111 of the device body 11 in a slipping manner such that slipping on the device body 11 is available, and thereby, the relative positions of the first electrode 2 and the second electrode 3 may be changed, so that measurement of physiological signal on various measurement sites on the human body is available. Therefore, the measurement patch device of the invention is applicable to making multi-lead physiological signal measurement on electrocardiography (referred to ECG hereinafter) or electromyography (referred to EMG hereinafter), and to the human bodies with different somatotypes, such as children, adults, males or females.

It should also be noted that the slipping body 12 of the measurement patch device 1 of the invention may slip on the device body 11. That is, the slipping body 12 may slip in a direction toward to or away from the device body 11. As the slipping body 12 slips toward to the device body 11, the overlapping level of the slipping body 12 and the device body 11 is increased gradually, such that the total length of the measurement patch device 1 will be reduced gradually. Accordingly, after the measurement patch device 1 of the invention has been used, the slipping body 12 may slip in the direction toward to the device body 11, such that the total length of the measurement patch device 1 is reduced for ease of accommodation or carrying.

A first identification mark 115 and a second identification mark 125 are arranged on the device body 11 and the slipping body 12 of the invention, respectively, for identifying a relative slipping level (or an overlapping level) of the slipping body 12 on the device body 11. As such, a user may reproduce an appropriate slipping level of the slipping body 12 on the device body 11 indicated by professional medical staff by using the first identification mark 115 and the second identification mark 125 although there is no assistance from professional medical staff, such that the relative position for the two electrodes of the measurement patch device is appropriate in order for effective subsequent measurement of physiological signal, so that the measurement patch device of the invention may be used at home.

Figure 3:
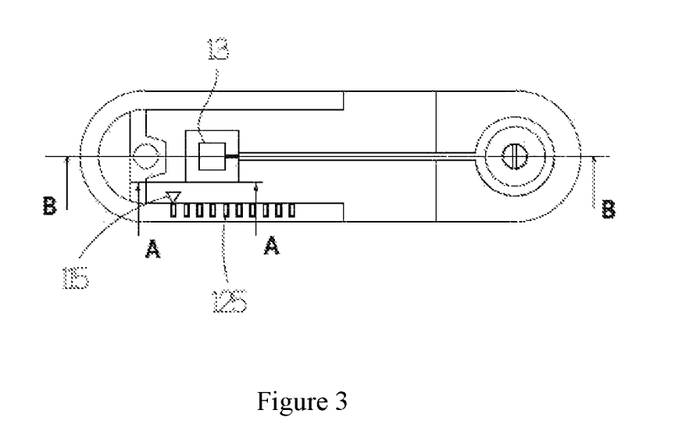
FIG. 3 is a top view of the measurement patch device shown in FIG. 1.

In the example shown in FIG. 3, the first identification mark 115 and the second identification mark 125 are rule scale and indicator, respectively, for the user to identify the slipping level of the slipping body 12 on the device body 11 distinctly. However, it is not limited thereto. In the invention, other mark forms may be selected as the first identification mark 115 and the second identification mark 125, and particularly, one or both of the first identification mark 115 and the second identification mark 125 may be omitted depending on actual use condition.

Figure 4:
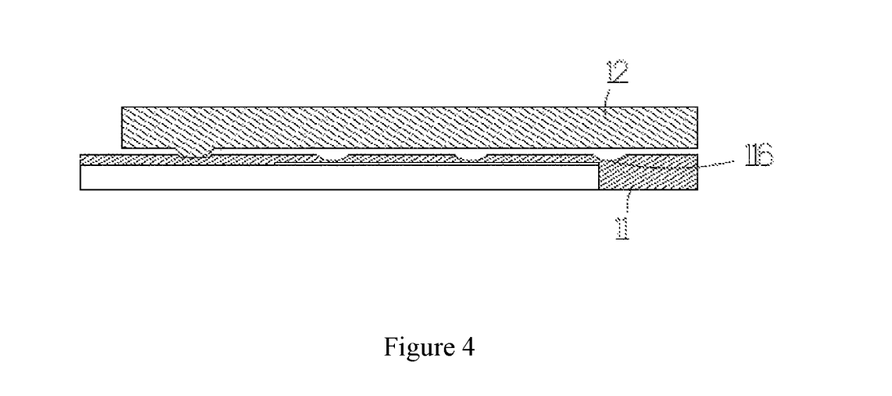
FIG. 4 is a cross-sectional view taken along line AA shown in FIG. 3.

Multiple positioning portions 116 are arranged equidistantly for the device body 11 capable of positioning the slipping body 12 to a particular position on the device body 11, respectively, such that the slipping level of the slipping body 12 on the device body 11 may be maintained in order for prevention the slipping body 12 from slipping in use process to influence effective measurement for physiological signal. In the example of FIG. 4, the positioning portions 116 are cavities, but are not limited thereto. The positioning portions 116 may also be bumps or other structures capable of constraining movement of the slipping body. In addition, a positioning structure in conjunction with the positioning portions 116 may be arranged on the slipping body 12.

The measurement patch device of the invention has further an electrically conductive elastomer 14 provided between the device body 11 and the slipping body 12. The electrically conductive elastomer 14 is, for example, an electrically conductive spring, which may be deformed with its own elasticity for the slipping body 12 and the device body 11 to slip relatively, and for two ends to maintain electrical contacts with the signal process module 13 and the second signal transfer layer 123, respectively, such that transfer for signal of the second signal transfer layer 123 to the signal process module 13 may be guaranteed as the slipping body 12 slips relative to the device body 11 for the signal process module 13 to perform analysis, process and wireless communication.

Refer to FIG. 5, a first joining portion 114 and a second joining portion 124 may be arranged for the device body 11 and the slipping body 12 of the invention, respectively. The first joining portion 114 is used to join the second joining portion of the slipping body of another set of measurement patch devices for the first signal transfer layer 113 of the device body 11 to be in electrical connection with the second signal transfer layer of the slipping body of the another set of measurement patch devices. The second joining portion 124 is used to join the first joining portion of the device body of the another set of measurement patch devices for the second signal transfer layer 123 in the slipping body 12 to be in electrical connection with the first signal transfer layer of the device body of the another set of measurement patch devices.

Figure 6:
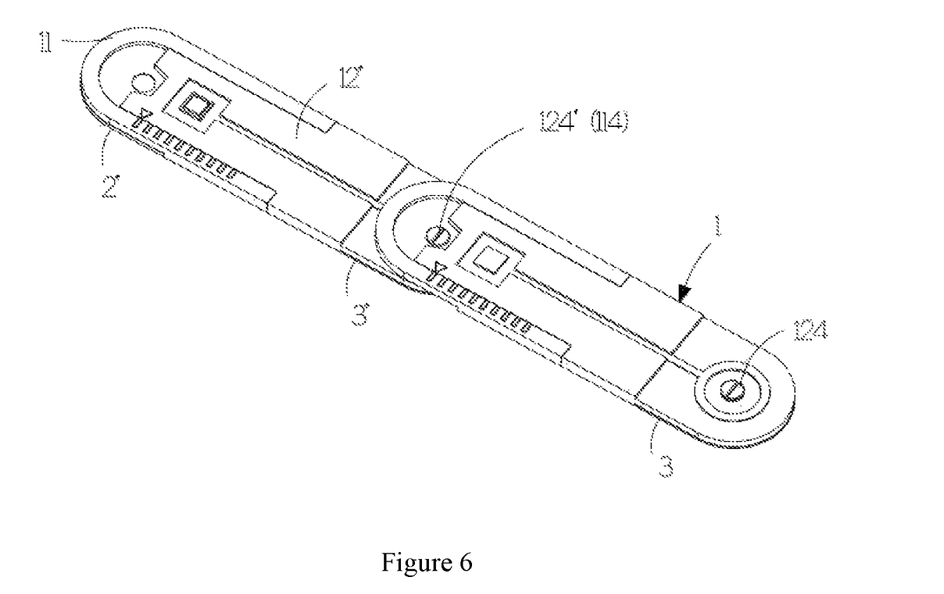
FIG. 6 is a schematic diagram showing a first combination state of two sets of measurement patch devices according to the invention.
Figure 7:
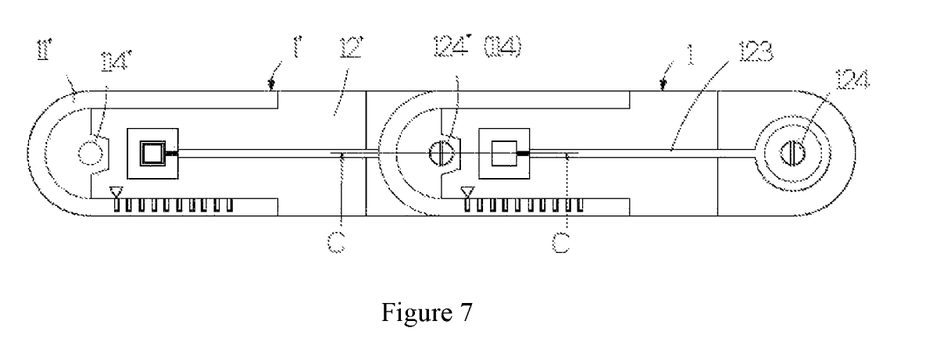
FIG. 7 is a top view of the measurement patch devices shown in FIG. 6.
Figure 8:
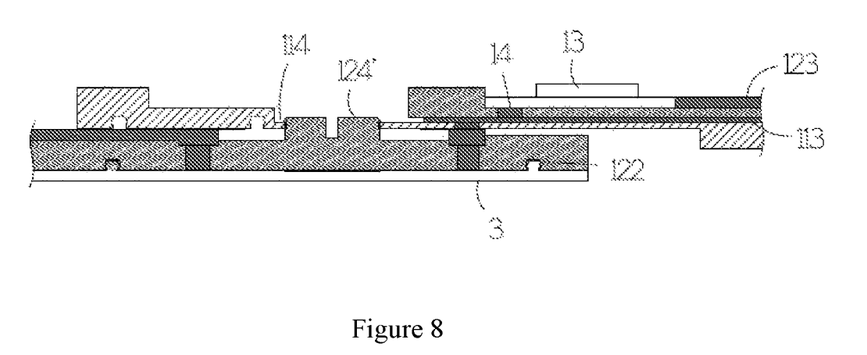
FIG. 8 is a cross-sectional view taken along line CC shown in FIG. 7.
Figure 11:
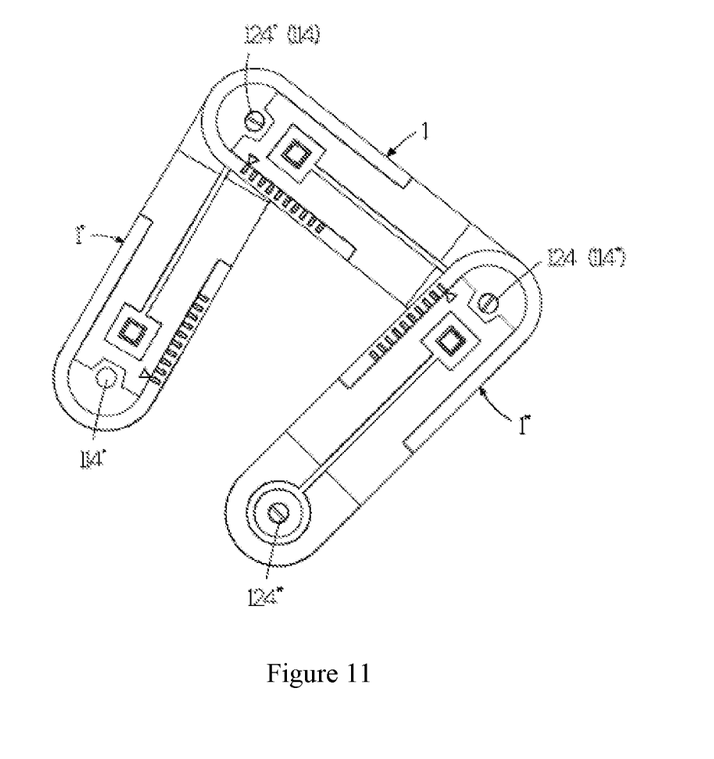
FIG. 11 is a schematic diagram showing a combination state of three sets of measurement patch devices according to the invention.

As shown in FIG. 6, a schematic diagram for a combination of two sets of measurement patch devices is shown. The first joining portion 114 of the device body 11 of the measurement patch device 1 is joined onto the second joining portion 124' of the slipping body 12' of another set of measurement patch devices 1'. There are total three electrodes 2', 3', 3 for the physiological signal measurement device formed after the measurement patch devices 1, 1' are joined, such that multi-channel and multi-lead physiological signal measurement is available on three measurement sites on the human body to save physiological signal measurement time. It should be noted additionally that, the first, second joining portions of the measurement patch device of the invention may further combine another set of measurement patch devices, respectively, as shown in FIG. 11. The first joining portion 114 of the measurement patch device 1 may combine the second joining portion 124' of the measurement patch device 1'. The second joining portion 124 of the measurement patch device 1 may combine the first joining portion 114" of the measurement patch device 1". The first joining portion 114' of the measurement patch device 1' may further combine the second joining portion 124" of the measurement patch device 1". Therefore, the number for combinations of the measurement patch devices of the invention is not limited to two sets mentioned above. Moreover, the number of electrodes after combination is not limited to three mentioned above.

Figure 9:
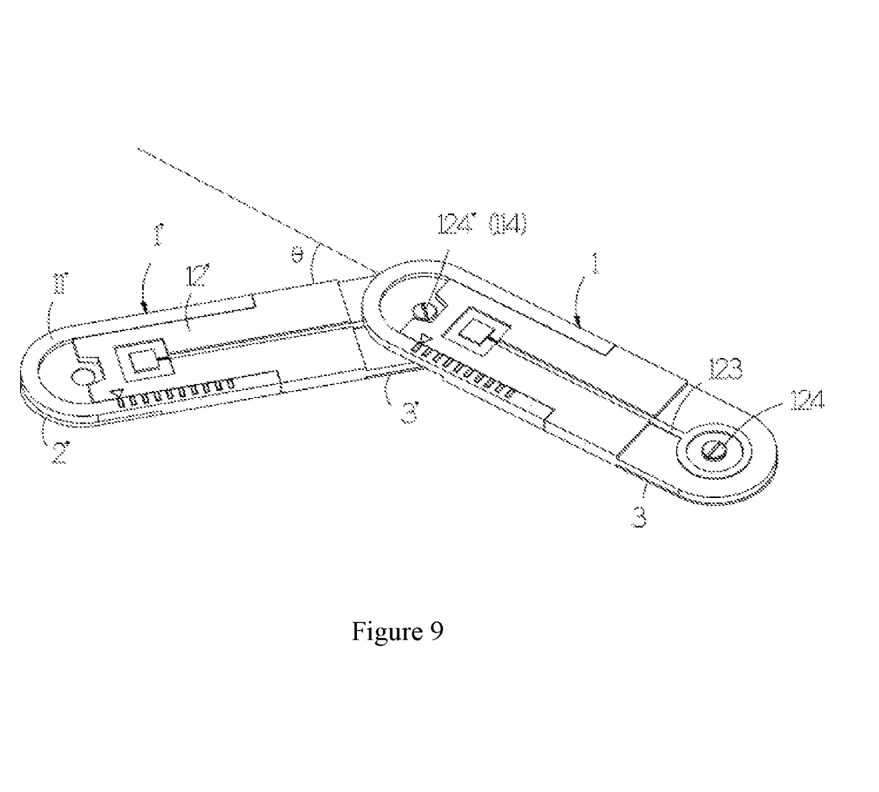
FIG. 9 is a schematic diagram showing a second combination state of two sets of measurement patch devices according to the invention.

The first, second joining portions 114, 124 on the device body 11 and the slipping body 12 of the invention may be an elastic tenon and a engagement hole with fitting structure, respectively for the two joined sets of measurement patch devices to rotate with respect to each other. The two sets of measurement patch devices as shown in FIG. 9 have an intersection angle marked as $\Theta$ after relative rotation to comply with the requirement for measurement of physiological signal on the human body.

In summary, there are at least the following characteristics for the measurement patch device of the invention:

1. The total length may be changed in accordance to use condition, such that there is effect of ease of carrying and accommodation, and measurement for physiological signal from various sites on the human body is available.

2. With the joining construction, integral joining with another set of measurement patch devices is available for multi-channel or multi-lead physiological signal measurement to save physiological signal measurement time.

3. The aforementioned joining construction may further provide two mutually joined sets of measurement patch devices which rotate with respect to each other for adaptation to measurement sites of the human body.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A measurement patch system having a plurality of identical measurement patch devices, each of the measurement patch devices having a first electrode and a second electrode for measuring a physiological signal, each of the measurement patch devices comprising:
   a device body having a guide rail formed thereon and having a first electrode bonding portion and a first signal transfer layer; the first electrode bonding portion bonding the first electrode and connecting electrically the first electrode and the first signal transfer layer;
   a slipping body provided on the guide rail of the device body in a slipping manner for slipping on the device body, the slipping body having an accommodation space formed therein and having a second electrode bonding portion and a second signal transfer layer; the second electrode bonding portion bonding the second electrode and connecting electrically the second electrode and the second signal transfer layer; and
   a signal process module accommodated in the accommodation space and configured for acquiring the physiological signal measured by the first and the second electrodes through the first and the second signal transfer layers, respectively, and for processing, analyzing and wirelessly communicating the acquired physiological signal,
   wherein the device body of each of the identical measurement patch devices further has a first joining portion that is used to join a slipping body of another one of the identical measurement patch devices for the first signal transfer layer of the device body to be in electrical connection with a second signal transfer layer of the slipping body of the another one of the identical measurement patch devices; and
   wherein the slipping body of each of the measurement patch devices further has a second joining portion; the second joining portion is configured to join a first joining portion of still another one of the identical measurement patch devices for the second signal transfer layer of the slipping body to be in electrical connection with a first signal transfer layer of the still another one of the identical measurement patch devices.

2. The measurement patch system according to claim 1, wherein each first and the second joining portions are an elastic tenon and an engagement hole with fitting structure, respectively.

3. The measurement patch system according to claim 1, wherein each first bonding portion is bonded with the first electrode in a manner selected from the group consisting of lock joint, fastening, magnetism, and adhesion; wherein each second bonding portion is bonded with the second electrode in a manner selected from the group consisting of lock joint, fastening, magnetism, and adhesion.

4. The measurement patch system according to claim 1, wherein each device body and each slipping body have a first identification mark and a second identification mark, respectively, for identifying an overlapping level of the slipping body on the device body.

5. The measurement patch system according to claim 1, wherein each device body has multiple positioning portions equidistantly for positioning the slipping body on the device body.

6. The measurement patch system according to claim 1, wherein each signal process module has an analog front-end signal detection unit and a digital signal processor, the analog front-end signal detection unit is used to acquire the physiological signal, and the digital signal processor is employed for feature extraction and classification of the physiological signal for processing and analyzing the physiological signal to convert the physiological signal into digital physiological information.

7. The measurement patch system according to claim 6, wherein each signal process module further has a digital controller, a storage unit, and a wireless transceiver, wherein the digital controller is used to provide communication between the digital signal processor and the wireless transceiver, the storage unit is used to store the acquired physiological signal and the processed and analyzed physiological information, and the wireless transceiver is used to communicate to a monitoring device by using a wireless communication technology.

8. The measurement patch system according to claim 1, wherein the acquired physiological signal is an electrocardiographic signal, an electromyographic signal, an electrooculographic signal, a temperature signal, a blood pressure signal, an impedance signal and/or a nerve conduction signal.

9. The measurement patch system according to claim 1, each measurement patch device further having an electrically conductive elastomer provided between the device body and the slipping body, two ends keeping in electrical contact with the signal process module and the second signal transfer layer, respectively, by means of elastic deformation.

* * * * *